(12) United States Patent
Weitzig et al.

(10) Patent No.: US 8,768,490 B2
(45) Date of Patent: Jul. 1, 2014

(54) ELECTRODE CATHETER, IN PARTICULAR FOR CARDIAC THERAPY

(71) Applicant: Biotronik SE & Co. KG, Berlin (DE)

(72) Inventors: Pierre Weitzig, Berlin (DE); Jochen Palm, Mahlow (DE); Detmar Jadwizak, Erkner (DE); Carsten Fruendt, Berlin (DE); Gordon Hillebrand, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/748,158

(22) Filed: Jan. 23, 2013

(65) Prior Publication Data

US 2013/0226274 A1    Aug. 29, 2013

Related U.S. Application Data

(60) Provisional application No. 61/603,959, filed on Feb. 28, 2012.

(51) Int. Cl.
*A61N 1/00* (2006.01)

(52) U.S. Cl.
USPC .......................................................... 607/122

(58) Field of Classification Search
USPC .......................................................... 607/122
See application file for complete search history.

(56) References Cited

U.S. PATENT DOCUMENTS

| 6,178,354 | B1 * | 1/2001 | Gibson | 607/116 |
| 6,882,886 | B1 | 4/2005 | Witte et al. | |
| 7,493,173 | B2 | 2/2009 | Geistert | |
| 2003/0023295 | A1 | 1/2003 | Osypka | |
| 2012/0071870 | A1 * | 3/2012 | Salahieh et al. | 606/33 |
| 2013/0274614 | A1 * | 10/2013 | Shimada et al. | 600/483 |

FOREIGN PATENT DOCUMENTS

| WO | 9742893 | 11/1997 |
| WO | 0032130 | 6/2000 |
| WO | 0103595 | 1/2001 |

OTHER PUBLICATIONS

Extended European Search Report and Notes to the European Search Report on European Patent Application No. EP 12 19 6257, dated Oct. 15, 2013 (10 pages).

European Search Report and Notes to the European Search Report on European Patent Application No. EP 12 19 6257, dated Jun. 13, 2013 (6 pages).

* cited by examiner

*Primary Examiner* — Robert N Wieland
(74) *Attorney, Agent, or Firm* — Buchanan Ingersoll & Rooney PC

(57) ABSTRACT

An electrode catheter, in particular for cardiac therapy, includes an elongated, tube-type catheter body, a ring electrode before the distal end of the electrode catheter for delivery and/or measurement of an electrical signal, in particular an electrocardio signal, by way of the outer electrode contact surface thereof, and a supply lead for the electrical connection of the ring electrode. The ring electrode is mounted on the catheter body such that it can be displaced relative thereto in the longitudinal axial direction.

14 Claims, 7 Drawing Sheets

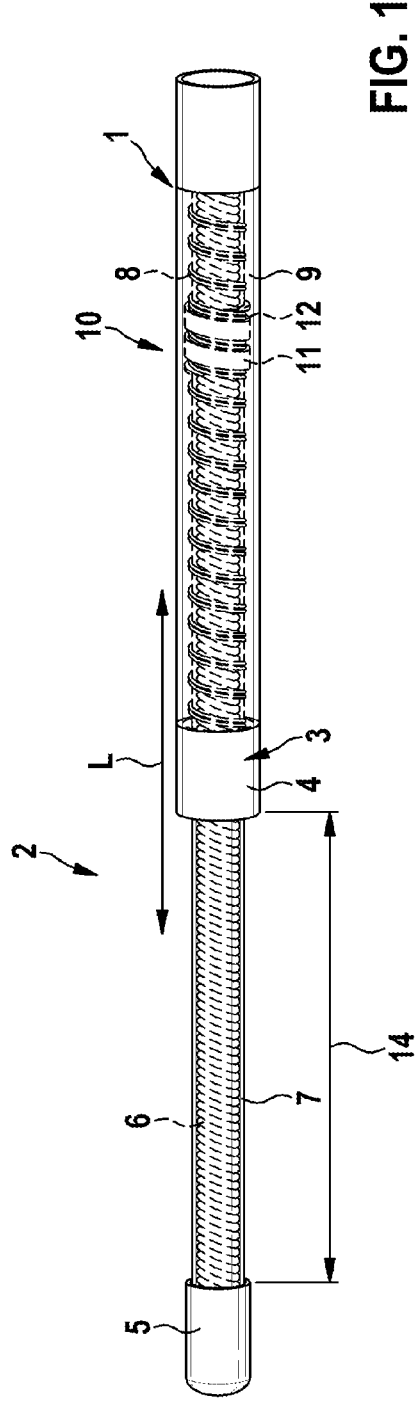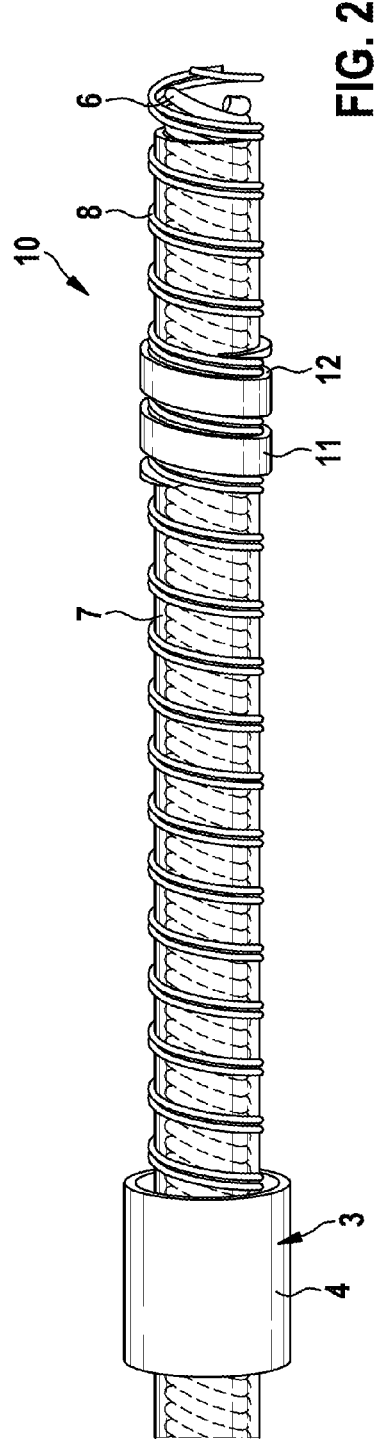

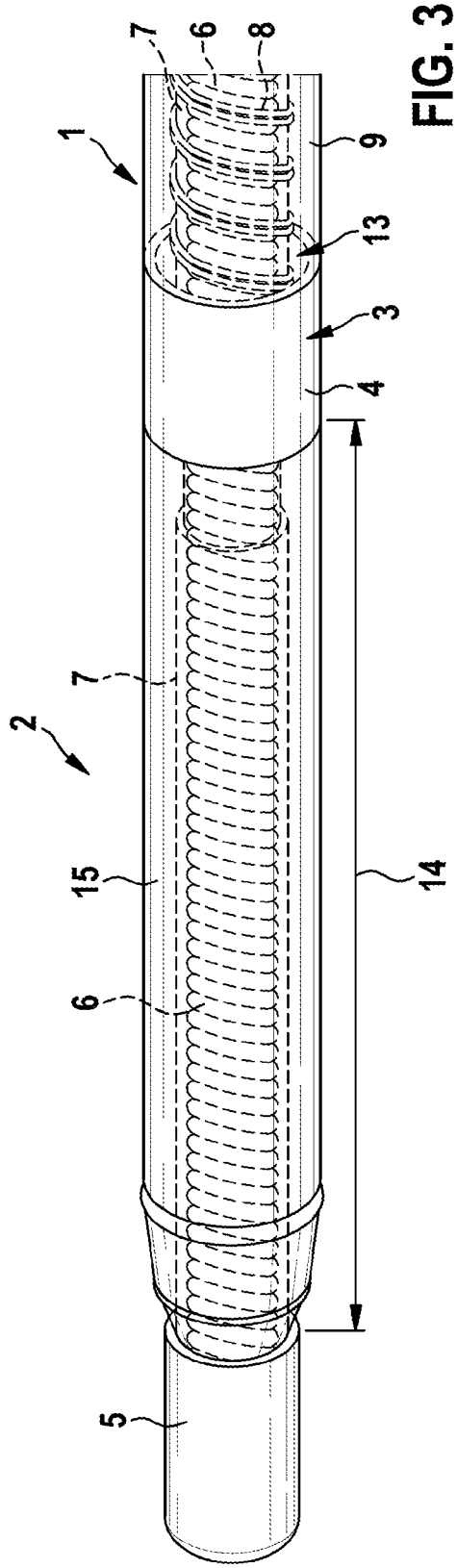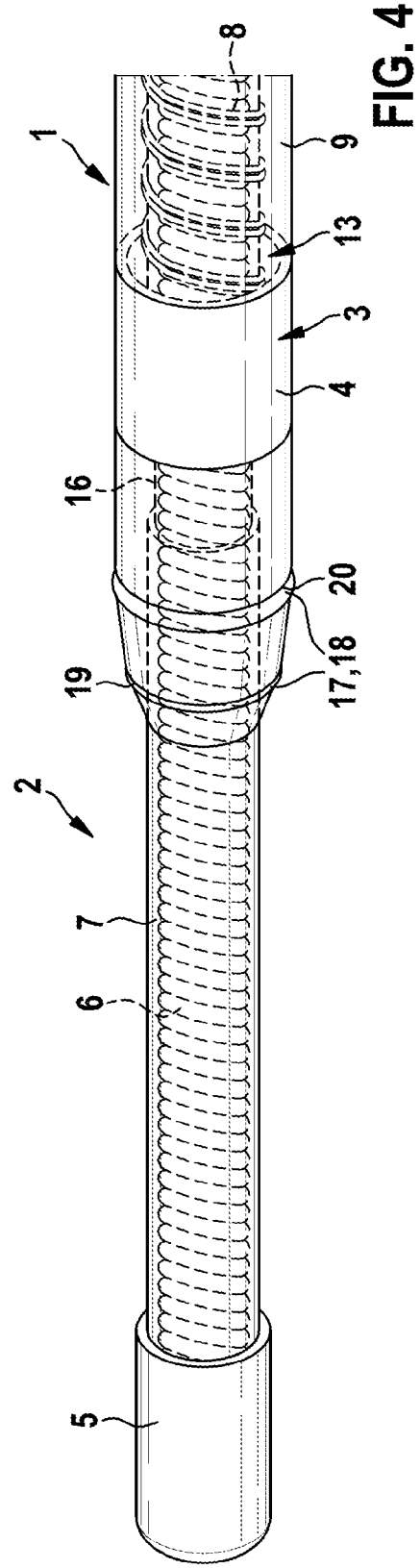

ELECTRODE CATHETER, IN PARTICULAR FOR CARDIAC THERAPY

CROSS-REFERENCE TO RELATED APPLICATIONS

This patent application claims the benefit of co-pending U.S. Provisional Patent Application No. 61/603,959, filed on Feb. 28, 2012, which is hereby incorporated by reference in its entirety.

TECHNICAL FIELD

The present invention generally relates to an electrode catheter and, in particular to an electrode catheter for cardiac therapy, which includes an elongated, tube-type catheter body, a ring electrode before the distal end of the electrode catheter for delivery and/or measurement of an electrical, in particular an electrocardio, signal by way of the outer electrode contact surface thereof, and a supply lead for the electrical connection of the ring electrode.

BACKGROUND

The above-mentioned features depict the simplest, basic configuration of an electrode catheter comprising a ring electrode, as made known in several prior art documents, such as, for example, U.S. Pat. No. 6,882,886 and/or U.S. Pat. No. 7,493,173. Such electrode catheters, which are also known as electrode leads designed to remain in the body permanently, generally comprise the ring electrode mentioned above, as well as a tip electrode in the case of a bipolar design, or further ring electrodes in the case of a multipolar electrode catheter.

A problem addressed by the present invention results from the requirements, which are partially contradictory, on the placement of an electrode catheter in a coronary artery, for example. For one, the electrode catheter should be implanted such that the catheter can be anchored as well as possible. The position identified as such by the implanting surgeon does not have to be the optimal position for achieving the best possible stimulation threshold values at the ring electrode. Another problem to be addressed is that, when stimulation catheters are used, unwanted phrenic stimulation (e.g., hiccup stimulation) can also occur, which so far can only be stopped per se by repositioning the ring electrode. This can result in impairment of the anchoring of the catheter.

An approach to a solution to of the above-identified problems, which is known from the prior art, is to provide a multipolar (e.g., four-poled) electrode lead in the case of which the tip electrode as well as three interspaced ring electrodes are provided. After implantation of the catheter, the particular ring electrode is used to measure electrocardio signals and/or deliver stimulating pulses that delivers the best results therefor in the particular anchoring position. A disadvantage of this configuration, however, is the fact that, since a plurality of ring electrodes are used, the design of the catheter is considerably more complex and a large number of cost-intensive components must be used that are no longer used in the practical application of the electrode.

The present invention is directed toward overcoming one or more of the above-identified problems.

Proceeding from at least the problems described above, an object of the present invention is therefore to improve an electrode catheter of the initially stated type in such a way that the anchoring thereof at the implantation site, as well as the positioning of the ring electrode, can be optimized with respect to signal-related aspects.

SUMMARY

At least the above object is achieved according to the present invention in that the ring electrode is mounted on the catheter body such that it is displaceable relative thereto in the axial direction.

Advantageously, once the electrode catheter has been positioned and affixed in a coronary artery, for example, the implanting surgeon is also able to vary the position of the ring electrode until the best stimulation threshold values are attained within the available displacement travel. The electrode catheter per se can remain at the anchoring point thereof, thereby making it possible to reduce the fixative forces caused by a displacement and, consequently, a threatened dislocation of the catheter. Even if phrenic stimulation should occur, the implanting surgeon can reposition the ring electrode without changing the position of the catheter itself, in order to prevent hiccup stimulation.

The ring electrode is preferably displaced by way of a drive device on the electrode catheter from the proximal end thereof, in the implanted state.

Highly diverse design concepts can be implemented for this drive device. For example, an alternative embodiment makes use of the connection coil, which is already present, provided for the electrical connection of the ring electrodes, which is then wound such that it is open at least along a partial length. In the sense of this patent application, "open" means that a defined space is present between the single wire of a coil section, which extends around 360° and is connected at the two ends thereof to the wire of the next coil section. This means that the wires are separated from one another. A so-called advancing element is disposed in the vicinity of the ring electrode, for example, in the region of the open winding, which is engaged with the connection coil in the space between the coil sections in such a way that rotation of the connection coil brings about a change in the length thereof and, therefore, axial displacement of the ring electrode. The connection coil of the ring electrode therefore performs a dual function in this configuration. The configuration of the drive device overall is relatively simple and reliable as a result. With respect to the great lengths of the catheter body and the connection coil, the changes in length of the coil that are achieved, in the range of a maximum of 40 to 50 mm, although more likely 20 to 30 mm in practical application, are not a problem. The spring forces that are generated remain low, thereby ensuring that the self-inhibition of the coil in the advancing element and, therefore, the constant retention of the position of the ring electrode, once set, are not impaired.

An easily modified variant for a drive device using the connection coil of the ring electrode is an embodiment in which the ring electrode has a threaded engagement with the windings of the connection coil by way of an internal thread and, therefore, rotation of the connection coil in the manner of a spindle induces an axial displacement of the ring electrode. In this embodiment, although the displacement motion of the ring electrode is more easily induced, it is not possible to utilize a bonded, electrical contact connection between the connection coil and the ring electrode, which can make the contacts less secure.

A further design variant for the embodiment of the drive device is based on a Bowden cable, in that pulling and pushing elements are routed from the proximal end of the electrode catheter to the ring electrode, i.e., cables which can be displaced in the lumen of the electrode catheter, for example.

According to a preferred development of the present invention, the outer tube of the electrode catheter, the length of which is flexible, adjusts its length in accordance with the axial displacement of the ring electrode. This is usually easily possible since this outer tube is usually made of a silicone material having a very high elasticity. Furthermore, the absolute length of the tube (e.g., 700 mm) is much greater than the displacement travel of the ring electrode and, therefore, the percentage change in length of the outer tube remains small.

A detailed problem associated with the structural implementation of the present invention is the sealing of the lumen of the outer tube, which accommodates the outer coil, against bodily fluids which enter the ring electrode from the distal side thereof.

An alternative for a solution of this detailed problem is to cover the distance between the ring electrode and the tip electrode of the electrode catheter with a tube piece which has a flexible length and is preferably bonded to the tip electrode. The zone is thereby hermetically closed, or sealed, distally from the ring electrode with respect to the outside, thereby ensuring that the seal is retained by way of the flexibility of the tube piece even if the ring electrode is displaced.

According to an alternative embodiment, in the case of an electrode catheter, the tip electrode of which is connected to the catheter body by way of an inner coil which is hermetically sealed by an inner tube, a short sealing tube piece can be placed distally, hermetically tight on the ring electrode, which rests on the inner tube in a sealing manner. The sealing effect thereof can be increased further by way of pressurizing rings, preferably such as shrink rings, placed thereon. These rings press the sealing tube piece radially against the inner tube.

According to a further alternative embodiment, the tube piece between the ring electrode and the tip electrode can be in the form of a bellows, which is tightly connected proximally to the ring electrode and distally to the tip electrode or the inner tube. Due to the bellows configuration, the bellows can adapt to the change in position of the ring electrode practically without resistance, and the change in length of the bellows takes place practically without application of additional force. This is advantageous with respect to smooth actuation of the drive device for the ring electrode. In addition, the seal integrity of any adhesion points between the bellows and the parts of the catheter supporting it is not impaired by forces acting thereon. Finally, the fold structure of the bellows also supports the affixation of the electrode catheter in a coronary artery.

According to a preferred embodiment of the bellows, the outer diameter of the bellows folds thereof corresponds to the outer diameter of the ring electrode. The electrode catheter is therefore optimally adapted to the implantation tools, since the insertion instrument is matched to the outer diameter of the catheter and, therefore, the electrodes thereof.

A particularly efficient design for the sealing of the lumen for the outer coil utilizes a sealing ring integrated in the ring electrode, which is inserted in the distally facing opening of the ring electrode between this and the inner tube of the electrode catheter. With respect to function, this inner sealing ring corresponds to an O-ring, as known from mechanical engineering. The positional accuracy and permanent fixation thereof can be further supported by an annular groove formed in the inner surface of the ring electrode, in which the sealing ring is seated. The tube piece, disposed distally before the ring electrode, can be omitted entirely in the aforementioned variant of the inner sealing ring. Possible warpage that may occur upon displacement of the ring electrode is therefore also prevented. Optionally, a system comprising a plurality of seals in the ring electrode inside one another in the axial direction, preferably each having weaker contact pressure, can be achieved. It is therefore possible to reduce the friction forces overall, to thereby simplify displacement of the ring electrodes on the inner tube.

To prevent twisting of the components which form the catheter body, the components are seated coaxially inside one another or are disposed in a row in the longitudinal axial direction, such as, for example, the outer tube, ring electrodes, inner tube and tube piece between the ring electrode and the tip electrode. It is provided according to a further preferred embodiment that the outer tube or the tube piece comprising the electrode are connected to the ring electrode by way of connecting sleeves which can rotate therein and engage in a sealing manner. A related rotation of the outer coil and the ring electrode is therefore not transferred to the outer tube and the tube piece. They are compressed or stretched only in the axial direction, which is gentler on material than twisting.

To ensure a clean longitudinal connection of the ring electrode to the outer tube and the tube piece toward the tip electrode, the connecting sleeves are connected at least indirectly to the ring electrode in a form-fit manner.

Finally, a particularly appropriate development for the electrical contacting of the ring electrodes is provided by way of the outer coil. The latter is connected to the ring electrode-side end thereof by way of a contact sleeve, which has electrical contact to the ring electrode, and which is preferably rotatably disposed between the ring electrodes and one of the connecting sleeves.

Low-friction surfaces on the inner tube, outer tube, tube piece and/or bellows can be created, in particular, by way of slide coatings.

Some of the advantages which can be achieved by way of the invention are summarized once more below:

- The best possible stimulation threshold values are obtained by way of the ring electrodes which are displaceable individually on the electrode catheter.
- When adjusting the position of the ring electrode, it is not necessary to displace the entire electrode catheter or the distal region of the electrode catheter, which is located in the coronary artery.
- The risk of dislocation after implantation is greatly reduced since the procedure to affix the electrode catheter in the coronary artery is separate from the procedure to optimize the position of the ring electrodes. It is therefore possible to always find a suitable horizontal position for the catheter having sufficient holding forces before the best possible placement for the ring electrode is set.
- No components are installed that are unnecessary or cost-intensive or are not used in actual applications, which is the case with quadrapolar electrodes, for example.
- Phrenic stimulation, which could possibly occur, can be prevented by repositioning the ring electrode without displacing the entire electrode catheter.

Further features, aspects, objects, advantages, and possible applications of the present invention will become apparent from a study of the exemplary embodiments and examples described below, in combination with the figures, and the appended claims.

DESCRIPTION OF THE DRAWINGS

Further features, details, and advantages of the present invention will be apparent from the following description which explains embodiments in greater detail with reference to the attached drawings. Shown are:

FIG. 1 illustrates the distal end region of an electrode catheter having a tip electrode and ring electrode, in a perspective view;

FIG. 2 illustrates an enlargement of a section of the Figure according to FIG. 1 without the outer tube in the region of the ring electrode comprising an outer coil;

FIGS. 3 and 4 are perspective partial views of the distal end region of an electrode catheter in two further embodiments;

DETAILED DESCRIPTION

Figure 5:
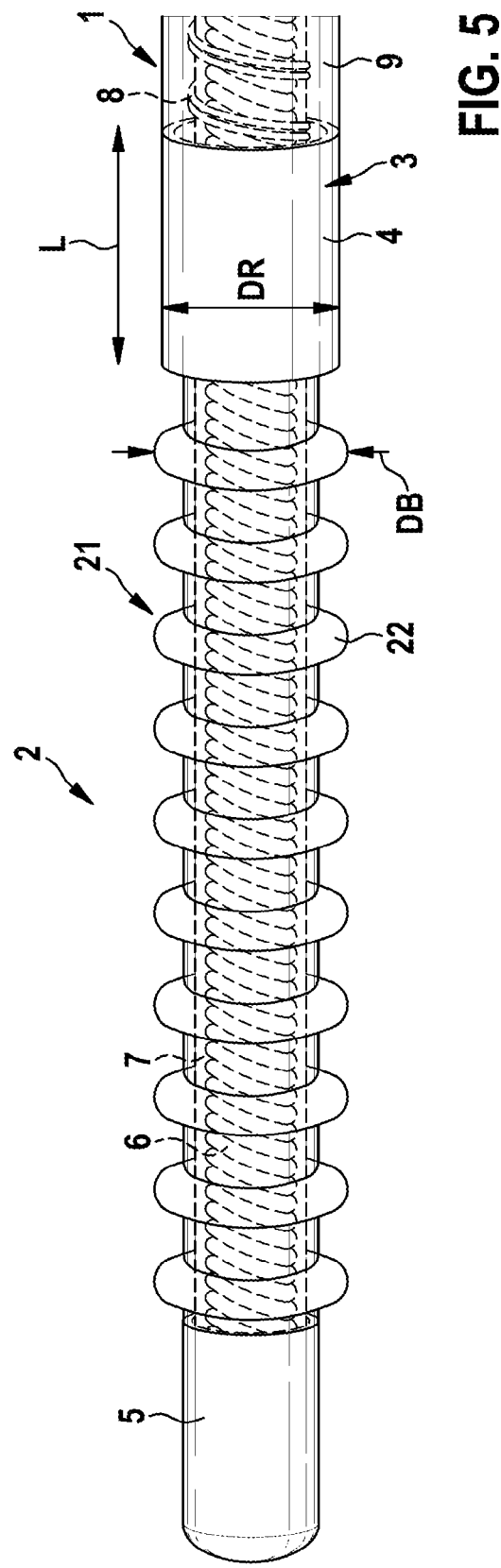
FIG. 5 is a view of an electrode catheter analogous to FIGS. 3 and 4 in further embodiments.

FIG. 1 shows the basic design of a bipolar electrode catheter that applies for all embodiments of the present invention described and depicted in the following. The electrode catheter comprises an elongated, tube-type catheter body 1 which is equipped on the proximal end thereof (not shown) with appropriate manipulation devices for handling the catheter and with electrical connections for contacting. The catheter body is equipped, in the region of the distal end 2 thereof, with a ring electrode 3 disposed before the distal end 2, which can serve to measure an electrocardio signal and/or deliver a related stimulation signal by way of the outer electrode contact surface 4 thereof. Furthermore, a tip electrode 5 is disposed on the distal end 2, which distally closes the catheter body 1 in the form of, for example, a cap or a cup.

An inner coil 6 is provided for the electrical connection of the tip electrode 5, which extends in an inner tube 7 through the entire catheter body 1 to the tip electrode 5, where it is fixed by way of conventional joining processes such as, for example, crimping, welding or soldering.

An outer coil 8 is seated on the inner tube 7, which extends to the ring electrode 3 and is connected thereto for the electrical contacting thereof. The catheter body 1 is closed with respect to the outside in the region of the outer coil 8 by way of an outer tube 9 made of, for example, flexible, highly stretchable silicone material. In all, the inner coil 6, inner tube 7, outer coil 8 and outer tube 9 are disposed coaxially inside one another.

A feature common to all embodiments is that the ring electrode 3 is displaceable in the longitudinal axial direction L along the catheter body 1 over a certain distance of 20 to 50 mm, for example. The displaceability is induced by way of a drive device labeled purely functionally as a whole with reference numeral 10, which can be actuated at a proximal end of the catheter body 1, which is not shown.

In the embodiment of an electrode catheter shown in FIGS. 1 and 2, this drive device 10 is embodied by the outer coil 8, which is openly wound at least in the region proximally before the ring electrode 3, in cooperation with an advancing element 11 fixedly mounted on the inner tube 7. This advancing element 11 is a sleeve which comprises a helical groove 12 corresponding to the winding pitch of the outer coil 8. As shown clearly in FIG. 2, the outer coil 8 extends across approximately two windings in this groove 12 of the advancing element 11. If the outer coil 8 is now set into rotation about the longitudinal axis thereof, displacement of the outer coil 8 in the longitudinal direction L is induced, which is transferred to the ring electrode 3. In the embodiment shown, the outer coil 8 is connected to the ring electrode in a bonded manner for this purpose, e.g., via soldering or welding, thereby ensuring that electrical contacting of the ring electrode 3 takes place in addition to the mechanical connection thereof.

The outer coil 8 is equipped on the proximal end, which is not shown, with a rotatable plug element which is gripped by the implanting surgeon and can be set into rotation. The rotary motion of the outer coil 8 can therefore be generated manually.

The various embodiments shown in FIGS. 3 to 8 are based on the design described with reference to FIGS. 1 and 2 with respect to the displacement of the ring electrode 3. The description will therefore not be repeated in this context.

The various embodiments according to FIGS. 3 to 8 are directed to the detailed problem of the sealing of the catheter body 1 in the region of the distal end 2 and the outer lumen 13, in particular, in which the outer coil 8 is routed to the ring electrode 3.

In the design shown in FIG. 3, the distance 14 between the ring electrode 3 and the tip electrode 5 is covered by a tube piece 15 which is disposed coaxially on the inner tube 7 and, in the unloaded state thereof, corresponds to the outer diameter of the ring electrode 3 and tip electrode 5. The material of this tube piece 15 can be a silicone having low hardness of 50 shore, for example. The front edge of the tube piece 15 facing the tip electrode 5 is bonded circumferentially to the inner tube 7, thereby sealing the inner space in accordance with proposal #1.

The tube piece 15 can be compressed by displacing the ring electrode 3 in the direction toward the tip electrode 5. The increase in diameter associated therewith can advantageously affect the fixation of the catheter in a cardiac vessel. Due to the low hardness of the tube piece 15, however, all stretching and compression processes can be implemented without application of considerable force, thereby ensuring that the adhesion sites of the tube piece 15 to the adjacent elements are not overstrained. In addition, the length of the tube piece 15 is so great anyway that the stretching processes are inconsequential relative thereto.

In the embodiment shown in FIG. 4, the lumen of the outer coil 8 comprising the inner space of the ring electrode 3 is sealed by a short sealing tube piece 16 which is bonded tightly at the proximal end thereof to the ring electrode 3. The sealing tube piece 16 extends conically toward the distal end thereof. The sealing on the inner tube 7, which encloses the inner coil 6 toward the tip electrode 5, is achieved by way of the internal stress of the sealing tube piece 16, and is strengthened by way of pressurizing rings 17, 18 in the form of shrink rings which are inserted in outer grooves 19, 20 of the sealing tube piece 16 and press the latter radially inwardly against the inner tube 7. As a result, when the ring electrode 3 rotates over the outer coil 8, accompanied by a longitudinal displacement of the ring electrode 3, torque is not transferred to the inner tube 7 to a notable extent. Instead, the sealing tube piece 16 glides on the inner tube 7.

Figure 6:
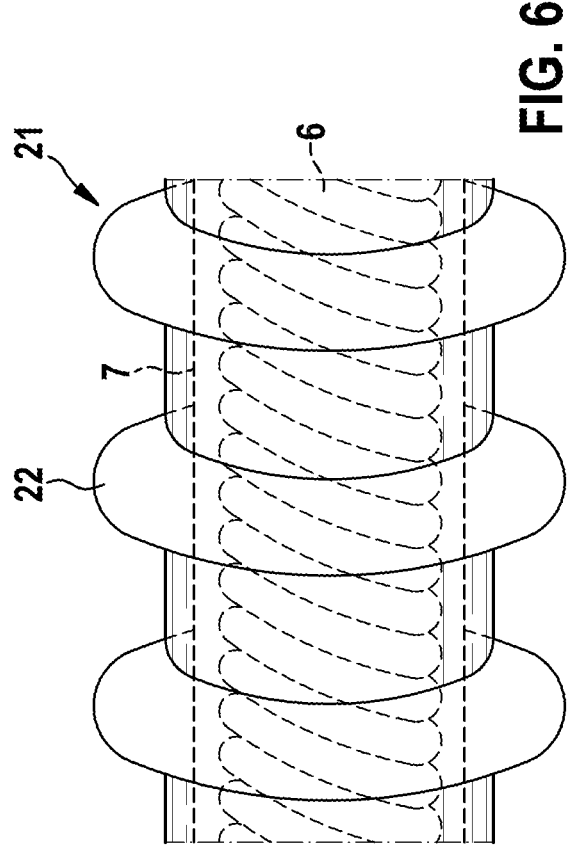
FIG. 6 is a sectional, partially exposed view of the electrode catheter according to FIG. 5 in the region of the bellows.

FIGS. 5 and 6 show an alternative to the tube piece 15 according to FIG. 3. The alternative is a bellows 21 made of, for example, silicone material, which is fixed by way of the end thereof facing the tip electrode 5 to the inner tube 7 by way of circumferential adhesion, and is connected in a hermetically sealed manner. Due to the highly flexible material of the bellows 21 and the inherent good stretchability of a bellows configuration, the bellows 21 can adapt by way of the length thereof to the change in position of the ring electrode 3 using a feasibly small amount of force. The outer diameter DB of the bellows folds 22 corresponds substantially to the outer diameter DR of the ring electrode 3, thereby ensuring problem-free insertability of the electrode catheter into the patient's body. The bellows folds 22 furthermore support the fixation of the catheter body 1 by way of the distal end 2 thereof in a cardiac vessel of the patient by way of the shape thereof.

Figure 7:
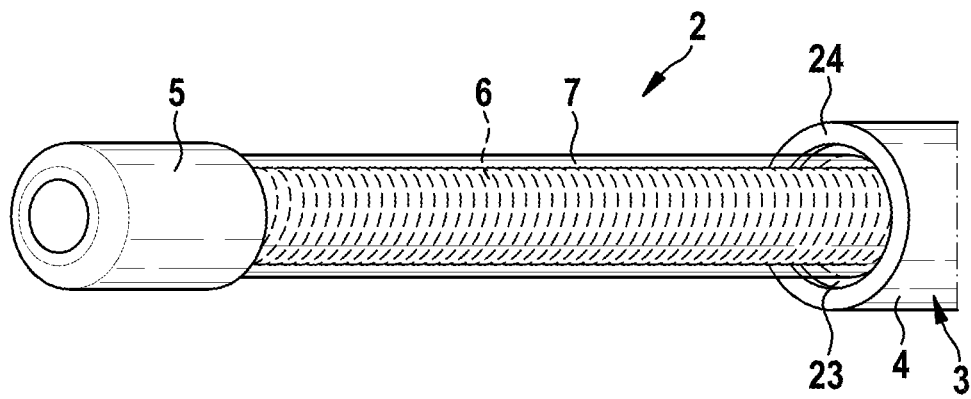
FIG. 7 is a perspective view of the distal end of an electrode catheter in a further embodiment.
Figure 8:
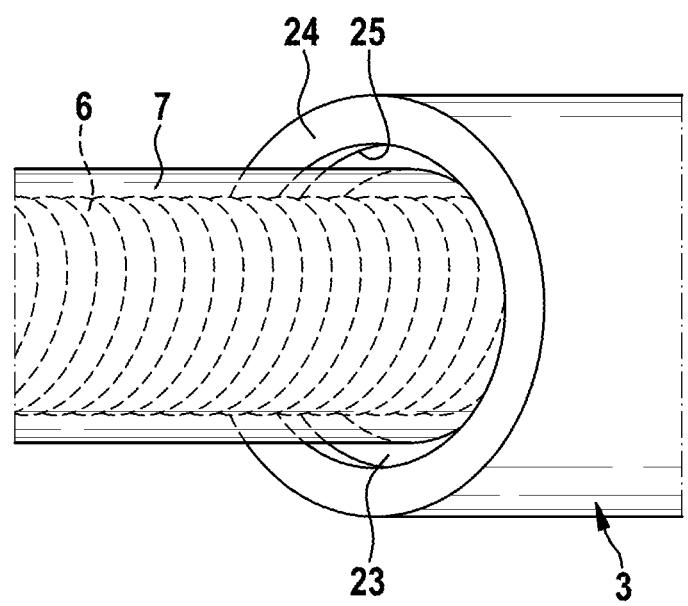
FIG. 8 is a perspective, sectional view of the electrode catheter according to FIG. 7.

A further embodiment of the catheter body 1 in the region of the distal end 2 thereof is shown in FIGS. 7 and 8. In this case, the inner coil 6, with the inner tube 7 thereof, extends to the tip electrode 5 without covering. The inner space of the ring electrode 3 and the outer tube 9 adjacent thereto in the proximal direction is sealed by way of one or more inner sealing rings 23 in the ring electrode 3. The inner sealing ring 23 is reliably affixed in the ring electrode in a circumferential inner groove 25 before the distally facing front edge 24. The inner sealing ring 23 is disposed tightly on the inner tube 7, thereby sealing the lumen region located there behind. If a plurality of inner sealing rings 23 is positioned one behind the other, each of the rings 23 can act on the inner tube 7 to a lesser extent, thereby reducing the friction forces and facilitating displacement of the ring electrode 3.

Figure 9:
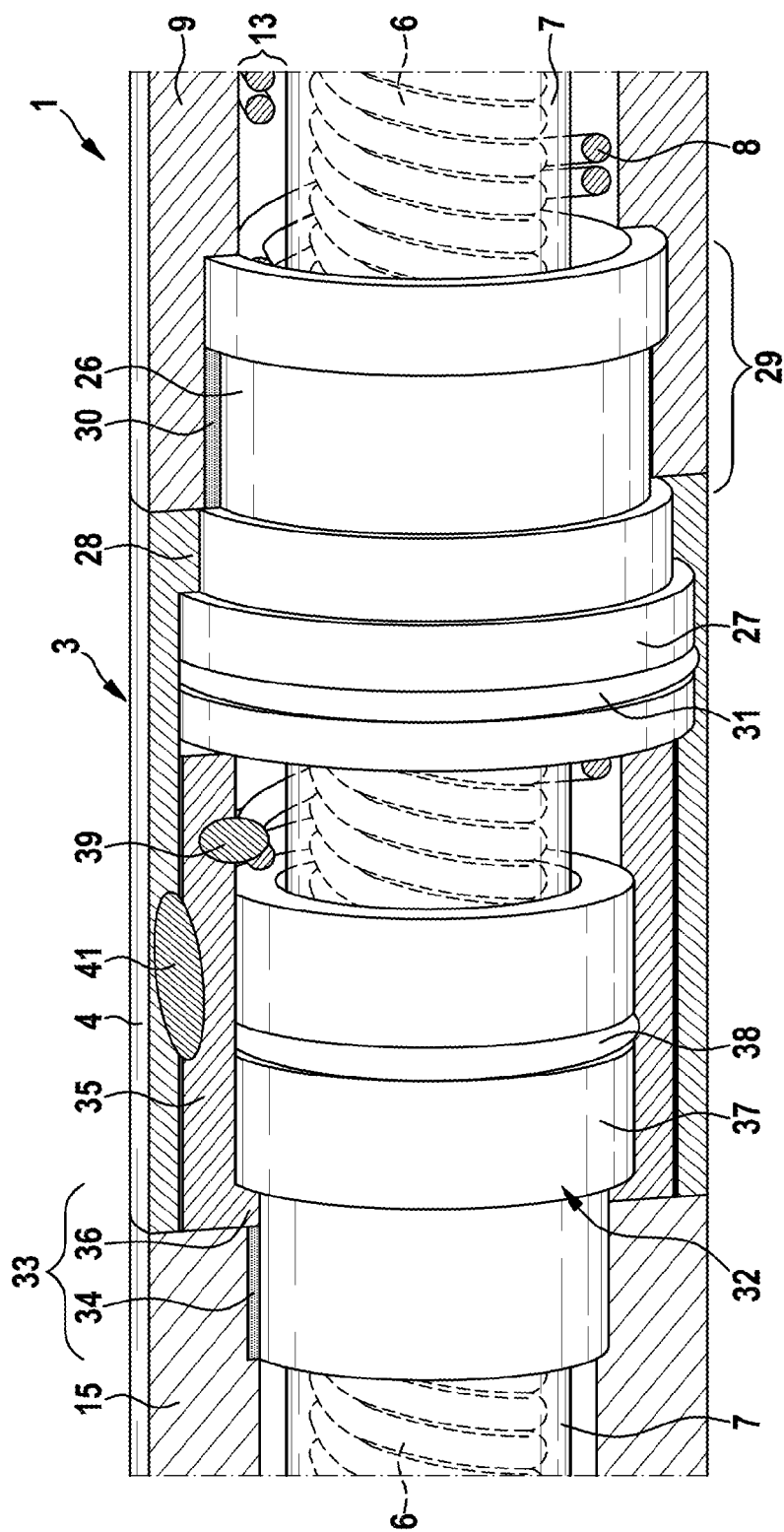
FIG. 9 is a perspective, partially exposed view of an electrode catheter comprising a connection of the ring electrode in a further alternative embodiment.
Figure 10:
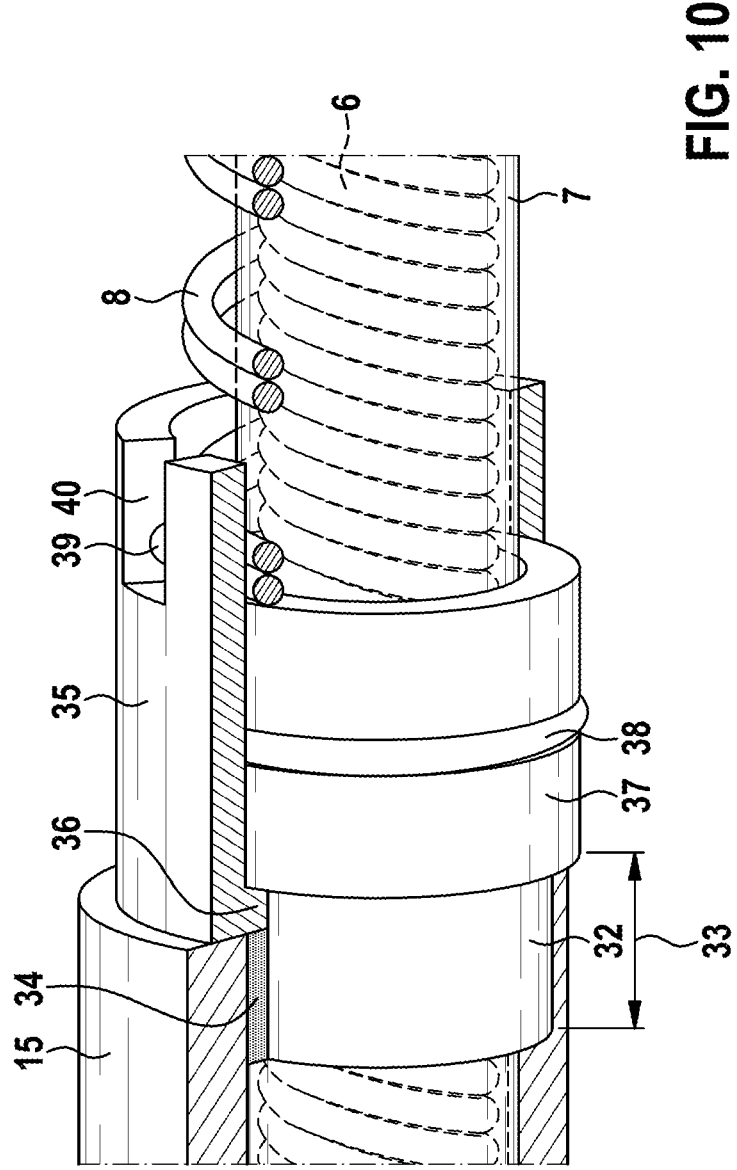
FIG. 10 is a perspective, partially exposed partial depiction of the connection of the distal tube piece to the ring electrode shown in FIG. 9.

The embodiment of an electrode catheter shown in FIGS. 9 and 10 solves the problem that fluid-tight transitions must be present between adjacent components, due to the rotation of the outer coil 8 for the longitudinal axial displacement of the ring electrode 3 using the advancing element 11 and the necessary sealing of the lumen of the electrode catheter; but the rotary motions would be transferred from the outer coil 8 and the ring electrode 3 to the adjacent tubes, such as, for example, the outer tube 9 and, in particular, the tube piece 15, if adhesion points were present. The twisting of these components associated therewith weakens material over time and should be avoided.

To solve this problem, in the case of the embodiment shown in FIGS. 9 and 10, the outer tube 9 is connected to the ring electrode 3 on the proximal side of the ring electrode 3 by way of a first connecting sleeve 26. For assembly, this connecting sleeve 26 is slid from the distal side into the ring electrode 3 and, with a distal ring shoulder 27, forms a stop for a proximal ring projection 28 on the proximal end of the ring electrode 3. The connecting sleeve 26 is therefore rotatably held in the ring electrode 3, in the longitudinal axial direction, but is held in a form-fit manner in the ring electrode 3 and cannot be retracted in the proximal direction.

The outer tube 9 is connected in a hermetically sealed manner to the cylindrical section 29 of the connecting sleeve 26, which projects from the ring electrode 3 in the proximal direction by way of bonding 30, thereby contributing to the sealing of the outer lumen 13. In addition, a sealing ring 31 is provided between the connecting sleeve 26 and the ring electrode 30 in the region of the ring shoulder 27, thereby sealing the inner space completely from the proximal side.

A connecting sleeve 32 is also provided toward the tube piece 15, the distal end of which projects from the ring electrode 3 in the distal direction. The proximal end of the tube piece 15 is fastened in a hermetically sealed manner on this corresponding cylindrical section 33 by way of a bonding 34.

A contact sleeve 35 is inserted between the part of the connecting sleeve 32 located in the ring electrode 3. The ring electrode 3, which, by way of an inwardly pointing ring projection 36, extends beyond a corresponding ring shoulder 37 of the connecting sleeve 32 from the distal side. The connecting sleeve 32 and the contact sleeve 35 are therefore coupled in a form-fit manner in the longitudinal axial direction in a manner analogous to the ring electrode 3 and the connecting sleeve 26. A further sealing ring 38 is inserted between the connecting sleeve 32 and the contact sleeve 35, which seals the inner space of the ring electrode 3 from the distal side with respect to the contact sleeve 35.

As shown clearly in FIG. 10, in particular, the contact sleeve 35 is connected mechanically and electrically to the distal end of the outer coil 8 by way of a welding 39 in a contact recess 40. At the same time, the contact sleeve 35 is connected mechanically and electrically to the ring electrode 3 by way of a further welding 41.

Due to the above-described design of the connection of the ring electrode 3, when the outer coil 8 is rotated, the contact sleeve 35, along with the ring electrode 3, is set into a rotary motion. As the same time, the outer coil 8 and, therefore, the contact sleeve 35 and the ring electrode 3 are displaced longitudinally axially by way of the advancing element 11 in order to adjust the position of the ring electrode 3. Due to the rotatable support of the connecting sleeves 26, 32, however, the rotary motion of the components is not transferred thereto or to the components bonded thereto, namely, the outer tube 9 and the tube piece 15, thereby ensuring they are not subjected to torque and, therefore, twisting. The inner regions of the catheter body are protected from penetration by fluids from the outside by way of appropriate sealing rings 31, 38.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An electrode catheter for cardiac therapy, comprising:
    an elongated, tube-type catheter body;
    a ring electrode disposed before a distal end of the electrode catheter for the delivery and/or measurement of an electrical electrocardio signal by way of an outer electrode contact surface thereof; and
    a supply lead for the electrical connection of the ring electrode,
    wherein the ring electrode is mounted on the catheter body such that it can be displaced relative thereto in a longitudinal axial direction,
    wherein the electrode catheter further comprises a drive device, by way of which the ring electrode can be displaced from a proximal end of the electrode catheter in the implanted state thereof, and
    wherein the drive device is formed by a connection coil of the ring electrode, which is wound openly at least on a partial length, wherein an advancing element located close before the ring electrode is engaged with the connection coil in the region of the open winding such that rotation of the connection coil induces a change in the length thereof and, therefore, axial displacement of the ring electrode.

2. An electrode catheter for cardiac therapy, comprising:
    an elongated, tube-type catheter body;
    a ring electrode disposed before a distal end of the electrode catheter for the delivery and/or measurement of an electrical electrocardio signal by way of an outer electrode contact surface thereof; and a supply lead for the electrical connection of the ring electrode, wherein the ring electrode is mounted on the catheter body such that it can be displaced relative thereto in a longitudinal axial direction, wherein the electrode catheter further comprises a drive device, by way of which the ring electrode can be displaced from a proximal end of the electrode catheter in the implanted state thereof, and wherein the drive device is formed by a connection coil of the ring electrode, wherein the ring electrode has threaded engagement with the windings of the connection coil by way of an inner thread and, therefore, rotation of the connection coil induces axial displacement of the ring electrode.

3. An electrode catheter for cardiac therapy, comprising:
an elongated, tube-type catheter body;
a ring electrode disposed before a distal end of the electrode catheter for the delivery and/or measurement of an electrical electrocardio signal by way of an outer electrode contact surface thereof; and
a supply lead for the electrical connection of the ring electrode,
wherein the ring electrode is mounted on the catheter body such that it can be displaced relative thereto in a longitudinal axial direction,
wherein the electrode catheter further comprises a drive device, by way of which the ring electrode can be displaced from a proximal end of the electrode catheter in the implanted state thereof, and
wherein the drive device is formed by pulling/pushing elements which are routed from the distal end of the electrode catheter to the ring electrode by cables which can be guided in a displaceable manner in a lumen of the catheter body.

4. An electrode catheter for cardiac therapy, comprising:
an elongated, tube-type catheter body;
a ring electrode disposed before a distal end of the electrode catheter for the delivery and/or measurement of an electrical electrocardio signal by way of an outer electrode contact surface thereof; and
a supply lead for the electrical connection of the ring electrode,
wherein the ring electrode is mounted on the catheter body such that it can be displaced relative thereto in a longitudinal axial direction, and
wherein the electrode catheter further comprises an inner tube and an outer tube, between which a connection coil of the ring electrode extends, wherein the outer tube has a flexible length and adapts its length in accordance with the axial displacement of the ring electrode.

5. An electrode catheter for cardiac therapy, comprising:
an elongated, tube-type catheter body;
a ring electrode disposed before a distal end of the electrode catheter for the delivery and/or measurement of an electrical electrocardio signal by way of an outer electrode contact surface thereof; and
a supply lead for the electrical connection of the ring electrode,
wherein the ring electrode is mounted on the catheter body such that it can be displaced relative thereto in a longitudinal axial direction, and
wherein the electrode catheter further comprises a tip electrode disposed distally before the ring electrode, wherein the distance between the ring electrode and the tip electrode is covered by a tube piece which has a flexible length and is bonded to the tip electrode.

6. An electrode catheter for cardiac therapy, comprising:
an elongated, tube-type catheter body;
a ring electrode disposed before a distal end of the electrode catheter for the delivery and/or measurement of an electrical electrocardio signal by way of an outer electrode contact surface thereof; and
a supply lead for the electrical connection of the ring electrode,
wherein the ring electrode is mounted on the catheter body such that it can be displaced relative thereto in a longitudinal axial direction, and
wherein the electrode catheter further comprises a tip electrode disposed distally before the ring electrode, wherein the tip electrode is connected to the catheter body by way of an inner coil which is hermetically sealed by an inner tube, wherein a sealing tube piece is placed on the ring electrode distally in a hermetically sealed manner and is mounted on the inner tube in a sealing manner.

7. The electrode catheter according to claim 6, wherein to strengthen the seal, pressurizing rings are placed on the sealing tube piece to apply radial pressure against the sealing tube piece.

8. The electrode catheter according to claim 7, wherein the pressurizing rings comprise shrink rings.

9. The electrode catheter according to claim 5, wherein the tube piece is in the form of a bellows which is tightly connected proximally to the ring electrode and distally to the tip electrode or the inner tube.

10. An electrode catheter for cardiac therapy, comprising:
an elongated, tube-type catheter body;
a ring electrode disposed before a distal end of the electrode catheter for the delivery and/or measurement of an electrical electrocardio signal by way of an outer electrode contact surface thereof; and
a supply lead for the electrical connection of the ring electrode,
wherein the ring electrode is mounted on the catheter body such that it can be displaced relative thereto in a longitudinal axial direction, and
wherein the electrode catheter further comprises at least one inner sealing ring, which is inserted in the distally facing opening of the ring electrode between this and the inner tube of the catheter body, which seals the lumen for the outer coil.

11. The electrode catheter according to claim 10, wherein each sealing ring is seated in an annular groove formed in the inner surface of the ring electrode.

12. An electrode catheter for cardiac therapy, comprising:
an elongated, tube-type catheter body;
a ring electrode disposed before a distal end of the electrode catheter for the delivery and/or measurement of an electrical electrocardio signal by way of an outer electrode contact surface thereof; and
a supply lead for the electrical connection of the ring electrode,
wherein the ring electrode is mounted on the catheter body such that it can be displaced relative thereto in a longitudinal axial direction, and
wherein an outer tube and/or a tube piece are connected to the ring electrode by way of connecting sleeves which can rotate therein and engage in a sealing manner.

13. The electrode catheter according to claim 12, wherein the connecting sleeves are connected at least indirectly in the longitudinal axial direction in a form-fit manner to the ring electrode.

14. The electrode catheter according to claim 12, wherein an outer coil is contacted to the ring electrode-side end thereof by way of a contact sleeve having electrical contact to the ring electrode, which is rotatably disposed between the ring electrode and one of the connecting sleeves.

* * * * *